(12) United States Patent
Kang et al.

(10) Patent No.: US 7,291,674 B2
(45) Date of Patent: Nov. 6, 2007

(54) SUPERABSORBENT POLYMER

(75) Inventors: Seungkoo Kang, Chapel Hill, NC (US);
Scott J. Smith, Greensboro, NC (US)

(73) Assignee: Stockhausen, Inc., Greensboro, NC (US)

( * ) Notice: Subject to any disclaimer, the term of this patent is extended or adjusted under 35 U.S.C. 154(b) by 214 days.

(21) Appl. No.: 10/695,060

(22) Filed: Oct. 28, 2003

(65) Prior Publication Data

US 2005/0090586 A1   Apr. 28, 2005

(51) Int. Cl.
*C08G 63/52* (2006.01)
*C08K 5/09* (2006.01)

(52) U.S. Cl. .................... 525/54.1; 525/78; 524/56; 524/58

(58) Field of Classification Search ............... 525/54.1, 525/78, 54.11; 524/56, 58
See application file for complete search history.

(56) References Cited

U.S. PATENT DOCUMENTS

| | | | |
|---|---|---|---|
| 5,496,933 A | 3/1996 | Kelkenberg et al. | |
| 5,599,916 A | 2/1997 | Dutkiewicz et al. | |
| 6,033,769 A | 3/2000 | Brueggemann et al. | |
| 6,072,101 A | 6/2000 | Beihoffer et al. | |
| 6,087,450 A | 7/2000 | Breitbach et al. | |
| 6,197,322 B1 | 3/2001 | Dutkiewicz et al. | |
| 6,524,508 B1 | 2/2003 | Ohnishi et al. | |
| 6,844,430 B2 * | 1/2005 | Pesce et al. ............ | 536/20 |
| 2003/0018312 A1 | 1/2003 | Pesce et al. | |
| 2003/0023216 A1 | 1/2003 | Carlucci et al. | |
| 2003/0049480 A1 | 3/2003 | Gagliardini et al. | |
| 2003/0111163 A1 | 6/2003 | Ko et al. | |
| 2003/0111774 A1 | 6/2003 | Kellenberger et al. | |
| 2003/0113463 A1 | 6/2003 | Ko et al. | |

FOREIGN PATENT DOCUMENTS

| | | |
|---|---|---|
| EP | 1149594 A1 | 10/2001 |
| WO | WO99/25393 | 5/1999 |
| WO | WO99/32697 | 7/1999 |
| WO | WO 01/00259 A1 | 1/2001 |

OTHER PUBLICATIONS

International Search Report mailed on Mar. 24, 2005 in PCT/US2004/035574.
Written Opinion of the International Searching Authority mailed on Mar. 24, 2005 in PCT/US2004/035574.

* cited by examiner

*Primary Examiner*—James J. Seidleck
*Assistant Examiner*—Olga Asinovsky
(74) *Attorney, Agent, or Firm*—Smith Moore LLP (57) ABSTRACT

The invention relates to a superabsorbent polymer comprising a composition comprising a polymeric resin composition comprising from about 55 to about 99.9 wt. % of polymerizable unsaturated acid group containing monomers, from about 0.001 to about 5.0 wt. % of internal crosslinking agent and from 0 to 25 wt % of a preneutralizing agent; wherein the polymeric resin composition is preneutralized from 0 to about 50 mole %; and a water swellable, water-insoluble aminopolysaccharide polymer wherein when the superabsorbent polymer is contacted with an aqueous solution, the polymeric resin composition is neutralized by the aminopolysaccharide polymer so that the superabsorbent polymer has a degree of neutralization of about 20 mole % or more than the preneutralization degree of the polymeric resin composition.

31 Claims, 3 Drawing Sheets

SUPERABSORBENT POLYMER

FIELD OF THE INVENTION

The invention relates to superabsorbent polymers, which absorb water, aqueous liquids and blood wherein the superabsorbent polymers of the present invention have improved properties, in particular high fluid retention and permeability properties. The present invention also relates to preparation of these superabsorbent polymers and their use as absorbents in hygiene articles.

BACKGROUND OF THE INVENTION

Superabsorbent refers to a water-swellable, water-insoluble, organic or inorganic material capable of absorbing at least about 10 times its weight and up to about 30 times its weight in an aqueous solution containing 0.9 weight percent sodium chloride solution in water. A superabsorbent polymer is a crosslinked neutralized polymer which is capable of absorbing large amounts of aqueous liquids and body fluids, such as urine or blood, with swelling and the formation of hydrogels, and of retaining them under a certain pressure in accordance with the general definition of superabsorbent.

The superabsorbent polymers that are currently commercially available include crosslinked polyacrylic acids or crosslinked starch-acrylic acid graft polymers, in which some of the carboxyl groups are neutralized with sodium hydroxide solution or potassium hydroxide solution. As a result of these absorbent properties, these polymers are chiefly used for incorporation into sanitary articles, such as babies' diapers, incontinence products or sanitary towels.

For fit, comfort and aesthetic reasons and from environmental aspects, there is an increasing trend to make sanitary articles smaller and thinner. This is being accomplished by reducing the content of the high volume fluff fiber of these articles. To ensure a constant total retention capacity of body fluids in the sanitary articles, more superabsorbent polymer content is being used in these sanitary articles. As a result of this, superabsorbent polymers must have increased permeability characteristics while retaining other characteristics such as adequate absorption and retention.

To obtain a superabsorbent polymer with high gel strength, the degree of crosslinking of the polymer may be increased, which necessarily results in a reduction in the swellability and the retention capacity. To achieve the increased permeabilities needed in extremely thin, next generation articles with low fiber content, current art has taught to increase the amount of covalent crosslinking to such high levels that the absorption and retention values of the superabsorbent polymers are reduced to undesirably low levels.

Aminopolysaccaride polymers include chitosan, a deacetylated chitin, is a cation-active, poly-primary amine with diverse applications in fields such as dispersing agents, adhesives, pesticides, wastewater treatment, food processing, and wound healing. Unfortunately, the known modified chitosan materials generally do not possess absorptive properties comparable to many of the synthetic, highly absorptive materials. This has prevented widespread use of such chitosan materials in absorbent personal care products.

It is therefore an object of the present invention to provide an absorbing polymer composition that exhibits excellent properties such as capabilities of maintaining high liquid permeability, hydrophilicity and liquid retention even when the superabsorbent polymer is increased in percent by weight based on the absorbent structure.

SUMMARY OF THE INVENTION

The present invention is directed to a superabsorbent polymer comprising a composition comprising a polymeric resin composition comprising from about 55 to about 99.9 wt. % of polymerizable unsaturated acid group containing monomers, from about 0.001 to about 5.0 wt. % of internal crosslinking agent and from 0 to 25 wt % of a preneutralizing agent wherein the polymeric resin composition is preneutralized from 0 to about 50 mole %; and a water swellable, water-insoluble aminopolysaccaride polymer wherein when the superabsorbent polymer is contacted with an aqueous solution, the polymeric resin composition is neutralized by the aminopolysaccaride polymer so that the superabsorbent polymer has a degree of neutralization of about 20 mole % or more than the preneutralization degree of the polymeric resin composition.

The present invention is also directed to a method of making the superabsorbent polymer comprising a composition comprising a polymeric resin composition comprising from about 55 to about 99.9 wt. % of polymerizable unsaturated acid group containing monomers, from about 0.001 to about 5.0 wt. % of internal crosslinking agent and from 0 to 25 wt % of a preneutralizing agent wherein the polymeric resin composition is preneutralized from 0 to about 50 mole %; and a water swellable, water-insoluble aminopolysaccaride polymer wherein when the superabsorbent polymer is contacted with an aqueous solution, the polymeric resin composition is neutralized by the aminopolysaccaride polymer so that the superabsorbent polymer has a degree of neutralization of about 20 mole % or more than the preneutralization degree of the polymeric resin composition.

The present invention is further directed to absorbent structures containing superabsorbent polymer comprising a polymeric resin composition comprising from about 55 to about 99.9 wt. % of polymerizable unsaturated acid group containing monomers, from about 0.001 to about 5.0 wt. % of internal crosslinking agent, and from 0 to 5.5 wt % of a preneutralizing agent wherein the polymeric resin composition is preneutralized from 0 to about 50 mole %; and a water swellable, water-insoluble aminopolysaccaride polymer; wherein when the superabsorbent polymer is contacted with an aqueous solution, the polymeric resin is neutralized by the aminopolysaccaride polymer so that the superabsorbent polymer has a degree of neutralization of about 20 mole % or more than the preneutralization degree of the polymeric resin composition.

DESCRIPTION OF THE PREFERRED EMBODIMENTS

A suitable superabsorbent polymer may be selected from natural, biodegradable, synthetic and modified natural polymers and materials. The term crosslinked used in reference to the superabsorbent polymer refers to any means for effectively rendering normally water-soluble materials substantially water-insoluble but swellable. Such a crosslinking means can include for example, physical entanglement, crystalline domains, covalent bonds, ionic complexes and associations, hydrophilic associations such as hydrogen bonding, hydrophobic associations or Van der Waals forces. Superabsorbent polymers include internal crosslinking and surface crosslinking.

One embodiment of the present invention is directed to a superabsorbent polymer comprising a composition comprising a polymeric resin composition comprising from about 55 to about 99.9 wt. % of polymerizable unsaturated acid group containing monomers, from about 0.001 to about 5.0 wt. % of internal crosslinking agent, and from 0 to 25 wt % of a preneutralizing agent wherein the polymeric resin composition is preneutralized from 0 to about 50 mole %; and a water swellable, water-insoluble aminopolysaccaride polymer wherein when the superabsorbent polymer is contacted with an aqueous solution, the polymeric resin composition is neutralized by the aminopolysaccaride polymer so that the superabsorbent polymer has a degree of neutralization of about 20 mole % or more than the preneutralization degree of the polymeric resin composition. In particular, the aminopolysaccaride polymer acts as a neutralization agent for the polymeric resin, reacting with the polymer resin composition to neutralize it to about 20 mole % or more, and preferably 30 mole % or more when the superabsorbent polymer is contacted with an aqueous solution, the polymeric resin is neutralized by the aminopolysaccaride polymer so that the superabsorbent polymer has a degree of neutralization of about 20 mole % or more than the preneutralization degree of the polymeric resin composition.

Another embodiment of the present invention is directed to a method of making the superabsorbent polymer comprising a composition comprising a polymeric resin composition comprising from about 55 to about 99.9 wt. % of polymerizable unsaturated acid group containing monomers, from about 0.001 to about 5.0 wt. % of internal crosslinking agent, and from 0 to 25 wt % of a preneutralizing agent wherein the polymeric resin composition is preneutralized from 0 to about 50 mole %; and a water swellable, water-insoluble aminopolysaccaride polymer wherein when the superabsorbent polymer is contacted with an aqueous solution, the polymeric resin composition is neutralized by the aminopolysaccaride polymer so that the superabsorbent polymer has a degree of neutralization of about 20 mole % or more than the preneutralization degree of the polymeric resin composition.

Another embodiment of the present invention is directed to absorbent structures containing superabsorbent polymer comprising a composition comprising a polymeric resin composition comprising from about 55 to about 99.9 wt. % of polymerizable unsaturated acid group containing monomers, from about 0.001 to about 5.0 wt. % of internal crosslinking agent, and from 0 to 25 wt % of a preneutralizing agent wherein the polymeric resin composition is preneutralized from 0 to about 50 mole %; and a water swellable, water-insoluble aminopolysaccaride polymer; wherein when the superabsorbent polymer is contacted with an aqueous solution, the polymeric resin is neutralized by the aminopolysaccaride polymer so that the superabsorbent polymer has a degree of neutralization of about 20 mole % or more than the preneutralization of the polymeric resin composition.

As used herein, a material will be considered to be water-soluble when it substantially dissolves in excess water to form a solution, thereby, losing its initially particulate form and becoming essentially molecularly dispersed throughout the water solution. As a general rule, the water-soluble chitosan salts will be free from a substantial degree of crosslinking, as crosslinking tends to render the chitosan water insoluble.

As used herein, the term "water-swellable, water-insoluble" is meant to refer to a material that, when exposed to an excess of a 0.9 weight percent solution of sodium chloride in water, swells to its equilibrium volume but does not dissolve into the solution. As such, a water-swellable, water-insoluble material generally retains its original identity or physical structure, but in a highly expanded state, during the absorption of the aqueous solution and, thus, must have sufficient physical integrity to resist flow and fusion with neighboring particles. A water-swellable, water-insoluble chitosan salt useful in the present invention is one which is effectively crosslinked to be substantially water insoluble but still is initially capable of absorbing at least about 14 times its own weight of a 0.9 weight percent solution of sodium chloride in water when under an applied load of about 0.3 pound per square inch.

An example of an aminopolysaccaride polymer include chitosan. The properties of chitosan relate to its polyelectrolyte and polymeric carbohydrate character. Thus, it is generally insoluble in water, in alkaline solutions at pH levels above about 6.5, or in organic solvents. In general, the amount of acid required to dissolve chitosan is approximately stoichiometric with the amino groups. Since the pKa for the amino groups present in chitosan is between 6.0 and 7.0, they can be protonated in very dilute acids or even close to neutral conditions, rendering a cationic nature to this biopolymer. This cationic nature is the basis of many of the benefits of chitosan. Indeed, chitosan material can be considered as a linear polyelectrolyte with a high charge density which can interact with negatively charged surfaces like anionic absorbent gelling materials present polymer.

Chitosan materials with a wide range of molecular weights are suitable for use in the present invention, typically chitosan materials for use herein have a molecular weight ranging from 1,000 to 10,000,000 grams per gram moles and more preferably from 2,000 to 1,000,000. Molecular weight means weight average molecular weight. Methods for determining the weight average molecular weight of chitosan materials are known to those skilled in the art. Typical methods include for example light scattering, intrinsic viscosity and gel permeation chromatography. It is generally most convenient to express the molecular weight of a chitosan material in terms of its viscosity in a 1.0 weight percent aqueous solution at 25° C. with a Brookfield viscometer. It is common to indirectly measure the viscosity of the chitosan material by measuring the viscosity of a corresponding chitosan salt, such as by using a 1.0 weight percent acetic acid aqueous solution. Chitosan materials suitable for use in the present invention will suitably have a viscosity in a 1.0 weight percent aqueous solution at 25° C. of from about 1 mPa s (1 centipoise) to about 80,000 mPa s (80,000 centipoise), more suitably from about 30 mPa s (30 centipoise) to about 10,000 mPa s (10,000 centipoise), even more suitably from 50 mPa s (50 centipoise) to about 1,000 mPa s (1,000 centipoise) and most suitably from 100 mPa s (100 centipoise) to about 500 mPa s (500 centipoise).

Chitosan materials of the present invention are available from VANSON located in Redmond Wash as standard grade Chitosan—polyamine having a high deacetylation to 95% and extra high molecular weight and particle size from about 200 to about 500 micron.

The superabsorbent polymer of the present invention is obtained by the initial preparation of a polymeric resin by the polymerization of from about 55 to about 99.9 wt. % of polymerizable unsaturated acid group containing monomers. Suitable monomers include those containing carboxyl groups, such as acrylic acid, methacrylic acid or 2-acrylamido-2-methylpropanesulfonic acid, or mixtures of these monomers are preferred here. It is preferable for at least about 50-weight.%, and more preferably at least about 75 wt. % of the acid groups to be carboxyl groups.

It may advantageous to preneutralize the polymeric resin composition with a separate preneutralization agent in the polmerization step and prior to the mixture of the polymeric resin composition and the aminopolysaccaride polymer. In particular, the acid groups are preneutralized to the extent of 0 to about 50 mole %, that is, the acid groups are preferably present as sodium, potassium or ammonium salts. The degree of preneutralization is preferably at least about 30 mole %. It is preferred to obtain polymers obtained by polymerization of acrylic acid or methacrylic acid, the carboxyl groups of which are preneutralized up to 50 mole %, in the presence of internal crosslinking agents. The acid groups are further neutralized, or post neutralized, after the polymer resin composition is mixed with the aminopolysaccaride polymer to form a superabsorbent polymer and the superabsorbent polymer is exposed to an aqueous solution. In particular, the acid groups are further neutralized by the aminopolysaccaride polymer to the extent of at least about 20 mole %, preferably 30 mole % to 80 mole %, that is the acid groups are present in salt form then the preneutralization degree of the polymeric resin composition.

Further monomers, which can be used for the preparation of the polymeric resins according to the present invention, are 0-40 wt. % of ethylenically unsaturated monomers which can be copolymerized with acrylamide, methacrylamide, hydroxyethyl acrylate, dimethylaminoalkyl (meth)-acrylate, ethoxylated (meth)-acrylates, dimethylaminopropylacrylamide or acrylamidopropyltrimethylammonium chloride. More than 40 wt. % of these monomers can impair the swellability of the polymers.

The internal crosslinking agent has at least two ethylenically unsaturated double bonds or one ethylenically unsaturated double bond and one functional group which is reactive towards acid groups of the polymerizable unsaturated acid group containing monomers or several functional groups which are reactive towards acid groups can be used as the internal crosslinking component and which is present during the polymerization of the polymerizable unsaturated acid group containing monomers.

Examples of internal crosslinking agents include aliphatic unsaturated amides, such as methylenebisacryl- or -methacrylamide or ethylenebisacrylamide, and furthermore aliphatic esters of polyols or alkoxylated polyols with ethylenically unsaturated acids, such as di(meth)acrylates or tri(meth)acrylates of butanediol or ethylene glycol, polyglycols or trimethylolpropane, di- and triacrylate esters of trimethylolpropane which is preferably oxyalkylated, preferably ethoxylated, with 1 to 30 mol of alkylene oxide, acrylate and methacrylate esters of glycerol and pentaerythritol and of glycerol and pentaerythritol oxyethylated with preferably 1 to 30 mol of ethylene oxide and furthermore allyl compounds, such as allyl (meth)acrylate, alkoxylated allyl (meth)acrylate reacted with preferably 1 to 30 mol of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid, and furthermore monomers which are capable of crosslinking, such as N-methylol compounds of unsaturated amides, such as of methylacrylamide or acrylamide, and the ethers derived therefrom. Ionic crosslinkers such as multivalent metal salts may also be employed. Mixtures of the crosslinking agents mentioned can also be employed. The content of the internal crosslinking agents is from about 0.01 to about 5 wt. %, and preferably from about 0.1 to about 3.0 wt. %, based on the total amount of the polymerizable unsaturated acid group containing monomers.

The superabsorbent polymers of the present invention may be surface crosslinked after polymerization. Surface crosslinking is any process that increases the crosslink density of the polymer matrix in the vicinity of the superabsorbent particle surface with respect to the crosslinking density of the particle interior. The superabsorbent polymers are typically surface crosslinked by the addition of a surface crosslinking agent. Preferred surface crosslinking agents include chemicals with one or more functional groups, which are reactive towards pendant groups of the polymer chains, typically the acid groups. The content of the surface crosslinking agents is from about 0.01 to about 5 wt. %, and preferably from about 0.1 to about 3.0 wt. %, based on the weight of the dry polymer. A heating step is preferred after addition of the surface crosslinking agent.

Preferably, the superabsorbent polymer of the present invention includes coating the superabsorbent polymer particle with a material such as ethylene glycol diglycidyl ether (EGDGE) followed by heating to effect surface crosslinking to improve the surface crosslinking density and the gel strength characteristics. More specifically, a surface crosslinking agent is coated onto the particulate by mixing the polymer with an aqueous alcoholic solution of the EGDGE surface cross linking agent. The amount of alcohol is determined by the solubility of the EGDGE and is kept as low as possible for technical reasons, for instance protection against explosions. Suitable alcohols are methanol, ethanol, acetone, butanol, or butyl glycol as well as mixtures of these alcohols. The preferred solvent is water, which typically is used in an amount of 0.3 to 5.0% by weight, relative to particulate superabsorbent polymer. In some instances, the EGDGE surface cross linking agent is dissolved in water, without any alcohol. It is also possible to apply the EDGDE surface cross linking agent from a powder mixture, for example, with an inorganic carrier material, such as $SiO_2$, or in the vapor state by sublimation of the EDGDE.

To achieve the desired surface cross linking properties, the EGDGE has to be distributed evenly on the particulate superabsorbent polymer. For this purpose, mixing is effected in suitable mixers, such as fluidized bed mixers, paddle mixers, milling rolls, or twin-worm mixers. It is also possible to carry out the coating of the particular superabsorbent polymer during one of the process steps in the production of the particulate superabsorbent polymer. A particularly suitable process for this purpose is the inverse suspension polymerization process.

The thermal treatment, which follows the coating treatment, is carried out as follows. In general, the thermal treatment is at a temperature between 100 and 300° C. If the preferred EGDGE is used, then the thermal treatment is at a temperature of about 100° C. for about 60 minutes. The treatment temperature depends on the dwell time and the kind of EGDGE. The thermal treatment may be carried out in conventional dryers, ovens, fluid bed driers, twin screw reactors and the like.

While particles are then used by way of example of the physical form of superabsorbent polymers, the invention is not limited to this form and is applicable to other forms such as fibers, foams, films, beads, rods and the like.

The superabsorbent polymer according to the invention can further comprise include from 0 to about 5 wt % of a multivalent metal salt, based on the weight of the mixture, on the surface of the polymer. The multivalent metal salt is preferably water soluble. Examples of preferred metal cations include the cations of Al, Fe, Zr, Mg and Zn. Preferably, the metal cation has a valence of at least +3, with Al being most preferred. Examples of preferred anions in the multivalent metal salt include halides, chlorohydrates, sulfates, nitrates and acetates, with chlorides, sulfates, chlorohydrates and acetates being preferred, chlorohydrates and sulfates being more preferred and sulfates being the most preferred. Aluminum sulfate is the most preferred multivalent metal salt and is readily commercially available. The preferred form of aluminum sulfate is hydrated aluminum sulfate, preferably aluminum sulfate having from 12 to 14 waters of hydration. Mixtures of multivalent metal salts can be employed.

The polymer and multivalent metal salt are mixed by dry blending, or preferably in solution, using means well known to those skilled in the art. Aqueous solutions are preferred. With dry blending, a binder may be employed in an amount sufficient to ensure that a substantially uniform mixture of the salt and the superabsorbent polymer is maintained. The binder may be water or a nonvolatile organic compound having a boiling point of at least 150° C. Examples of binders include water, polyols such as propylene glycol, glycerin and poly(ethylene glycol).

The superabsorbent polymers according to the invention may further include from 0 to about 5 wt % of water-insoluble, inorganic powder. Examples of insoluble, inorganic powders include silicon dioxide, silicic acid, silicates, titanium dioxide, aluminum oxide, magnesium oxide, zinc oxide, talc, calcium phosphate, clays, diatomataceous earth, zeolites, bentonite, kaolin, hydrotalcite, activated clays, etc. The insoluble inorganic powder additive may be a single compound or a mixture of compounds selected from the above list. Of all these examples, microscopic noncrystal silicon dioxide or aluminum oxide preferred. Further, a preferred particle diameter of the inorganic powder is 1,000 µm or smaller, and more preferably 100 µm or smaller.

The superabsorbent polymer according to the invention may also include the addition of from 0 to about 5 wt % of a surfactant to the polymer particle surface. It is preferred that these be added immediately prior to, during or immediately after the surface crosslinking step. Examples of such surfactants include anionic, non-ionic, cationic and amphoteric surface active agents, such as fatty acid salts, coco amines and amides and their salts, alkylsulfuric ester salts, alkylbenzene sulfonic acid salts, dialkyl sulfo-succinate, alkyl phosphate salt, and polyoxyethylene alkyl sulfate salt; polyoxyethylene alkyl ether, polyoxyethylene alkyl phenol ether, polyoxyethylene fatty acid ester, sorbitan fatty acid ester, polyoxy sorbitan fatty acid ester, polyoxyethylene alkylamine, fatty acid esters, and oxyethylene-oxypropylene block polymer; alkyl amine salts, quaternary ammonium salts; and lauryl dimethylamine oxide. However, it is not necessary to restrict the surfactant to those mentioned above. Such surfactants may be used individually, or in combination.

The superabsorbent polymers may also include from 0 to about 30 wt. % of water-soluble polymers, such as partly or completely hydrolysed polyvinyl acetate, polyvinylpyrrolidone, starch or starch derivatives, polyglycols or polyacrylic acids, preferably in polymerized-in form. The molecular weight of these polymers is not critical as long as they are water-soluble. Preferred water-soluble polymers are starch and polyvinyl alcohol.

It is sometimes desirable to employ surface additives that perform several roles during surface modifications. For example, a single additive may be a surfactant, viscosity modifier and react to crosslink polymer chains.

The superabsorbent polymers may also include from 0 to about 2.0 wt % of dedusting agents, such as hydrophilic and hydrophobic dedusting agents such as those described in U.S. Pat. Nos. 6,090,875 and 5,994,440 may also be employed in the process of the invention.

Further additives of the chitosan superabsorbent polymers according to the invention may include odor-binding substances, such as cyclodextrins, zeolites, inorganic or organic salts and similar materials; anti-caking additives, flow modification agents and the like.

The superabsorbent polymer according to the present invention is preferably prepared by first preparing the polymeric resin composition followed by mixing the dry polymeric resin particles with wet aminopolysaccaride polymer. The mixture is extruded and dried at about 110° C. for about 60 minutes, ground and sized through sieves to obtain the desired particle sizes.

The polymeric resin composition can be prepared by two methods although there are other methods that can be used. The polymeric resin composition can be prepared continuously or discontinuously in a large-scale industrial manner by the above-mentioned known process, the after-crosslinking according to the invention being carried out accordingly.

According to the first method, the partly neutralized monomer, preferably acrylic acid, is converted into a gel by free-radical polymerization in aqueous solution in the presence of crosslinking agents and optionally further components, and the gel is comminuted, dried, ground and sieved off to the desired particle size. This solution polymerization can be carried out continuously or discontinuously.

Inverse suspension and emulsion polymerization can also be used for preparation of the products according to the invention. According to these processes, an aqueous, partly neutralized solution of monomers, preferably acrylic acid, is dispersed in a hydrophobic, organic solvent with the aid of protective colloids and/or emulsifiers and the polymerization is started by free radical initiators. The internal crosslinking agents either are dissolved in the monomer solution and are metered in together with this, or are added separately and optionally during the polymerization. The addition of a water-soluble polymer as the graft base optionally takes place via the monomer solution or by direct introduction into the oily phase. The water is then removed azeotropically from the mixture and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

In one embodiment, the polymeric resin composition is used in the form of discrete particles. Superabsorbent polymer particles can be of any suitable shape, for example, spiral or semi-spiral, cubic, rod-like, polyhedral etc. Particle shapes having a large greatest dimension/smallest dimension ratio, like needles, flakes or fibers are also contemplated for use herein. Conglomerates of particles of superabsorbent polymers my also be used.

The polymeric resin composition is mixed with the wet chitosan-polyamine particles, 30% Chitosan mixed with 70% deionized water. The chitosan-polymaine is available from Vanson as a standard grade chitosan. The ratio of the polymeric resin to chitosan may range from 5:1 to 1:5. The resulting mixture was extruded, dried at 110° C. forced-air oven for 60 minute, ground and sized through sieves to obtain the desired particles sizes having a mean particle size of of about 300 microns.

The chitosan superabsorbent polymers may be surface treated by making a solution by admixing Ethylene Glycol Diglycidyl Ether (EGDGE), acetone and de-ionized water. To the solution is added dry Chitosan SAP precursors were placed in a mixer, and stirred at a sufficient speed to spread the SAP particle in mixer. The surface-treating solution was driven out by air-forced spray gun, and spread to the chitosan SAP particle. These coated Chitosan SAP particles are dried at 100° C. for 60 minute, and ground and sized through sieves to obtain the desired particles sizes.

Test Methods

Centrifuge Retention Capacity Test

The Centrifuge Retention Capacity (CRC) Test measures the ability of the superabsorbent polymer to retain liquid therein after being saturated and subjected to centrifugation under controlled conditions. The resultant retention capacity is stated as grams of liquid retained per gram weight of the sample (g/g). The sample to be tested is prepared from particles which is pre-screened through a U.S. standard 30 mesh screen and retained on a U.S. standard 50 mesh screen. As a result, the superabsorbent polymer sample comprises particles sized in the range of about 300 to about 600 microns. The particles can be pre-screened by hand or automatically.

The retention capacity is measured by placing about 0.2 grams of the pre-screened superabsorbent polymer sample into a water-permeable bag that will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is place in the pouch, the remaining open edge of the pouch is also heat-sealed. Empty bags are also made to serve as controls. Three samples are prepared for each superabsorbent polymer to be tested.

The sealed bags are placed submerged in a pan or the test solution at 23° C., making sure that the bags are held down until they are completely wetted. After wetting, the samples remain in the solution for about 30 minutes, at which time they are removed from the solution and temporarily laid on a non-absorbent flat surface.

The wet bags are then placed into the basket of a suitable centrifuge capable of subjecting the samples to a g-force of about 350. One suitable centrifuge is a clay Adams Dynac II, model #0103, having a water collection basket, a digital rpm gauge, and a machined drainage basket adapted to hold and drain the flat bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the superabsorbent polymer samples. The amount of solution retained by the superabsorbent polymer sample, taking into account the solution retained by the bag itself, is the centrifuge retention capacity (CRC) of the superabsorbent polymer, expressed as grams of fluid per gram of superabsorbent polymer. More particularly, the retention capacity is determined as:

(sample/bag after centrifuge−empty bag after centrifuge−dry sample weight)/dry sample weight The three samples are tested and the results are averaged to determine the retention capacity (CRC) of the superabsorbent polymer.

Extractable Polymer Content Determination

Extractable polymer content of carboxylic acid-based hydrogel-forming material is determined by admixing the hydrogel-forming polymer with synthetic urine for a period of time sufficient to substantially approach equilibrium with respect to extraction of polymer material from the hydrogel which is formed. The hydrogel/urine mixture is allowed to settle and a portion thereof is filtered. An aliquot of this filtrate is then taken, and the free acid groups on the polymer material dissolved in this filtrate are titrated to pH 10 with base. All of the carboxylate groups are then titrated to pH 2.7 with acid. These titration data are then used to calculate the amount of extractable polymer in the hydrogel-forming polymer sample.

(a) Preparation of the Extractable Polymer-Containing Filtrate Samples 1. 0.40 to 0.41 g of hydrogel-forming polymer is accurately (to .+−. 0.1 mg) weighed into a 150 ml disposable beaker. If glass beakers are used, they must be acid washed prior to use. (Glassware should be washed three times with dilute Hcl [conc. Hcl diluted 1:4 with distilled water], then three times with distilled water. This procedure removes traces of detergents and other contaminants which would otherwise interfere with the titration.)

2. 75 ml of synthetic urine are added. The synthetic urine composition referenced herein includes 970.77 g of completely demineralized water, 8.30 g of sodium chloride, 0.60 g of calcium chloride, 0.93 g of magnesium sulfate with 6 molecules of water of crystallization and 19.40 g of urea. The solution is finally diluted to one liter.

3. Samples are slowly stirred for a period of time sufficient to reach equilibrium. Equilibrium is generally reached within 16 hours. If extractable polymer content is to be measured as a function of time, for 1 hour in the present case, to define the extractables.

4. Samples are allowed to settle for 15 minutes.

5. Using a 3 ml disposable syringe and 0.22 micron filters, enough solution is filtered so that a 20 ml aliquot can be taken.

(b) Titration Conditions

1. If the titrations are to be performed manually, great care must be taken to assure that equilibrium is reached after each addition of titrant.

2. A 20 ml aliquot of the filtrate is transferred to a 50 ml disposable beaker. If glass beakers are being used, they must be acid washed prior to use as noted hereinbefore.

3. The aliquot is titrated to pH 10 with 0.1N NaOH.

4. The aliquot is then back titrated to pH 2.7 with 0.1N Hcl.

5. Steps 3 and 4 are performed on 20 ml of synthetic urine to obtain titration blanks for both steps of the titration.

(c) Calculations

1. The amount of polymerized acid moieties (e.g., acrylic acid) (in millimoles) in the supernatant aliquot ($M_a$) is given by:

$$M_a = (V_a - V_{ab})N_a \text{ millimoles } (mm)$$

where:

$V_a$=The volume (in ml) of acid required to titrate the aliquot to pH 10.

$V_{ab}$=The volume (in ml) of acid required to titrate 20 ml of synthetic urine to pH 10.

$N_a$=The normality (in meq/ml) of the acid (nominally 0.10 meq/ml)

2. The total amount of polymerized acid moieties (e.g. acrylic acid) plus polymerized neutralized acid moieties (e.g., sodium acrylate) (in mm) in the supernatant aliquot ($M_t$) is given by:

$$M_t = (V_b - V_{bb})N_b \text{ millimoles}$$

where:

$V_b$=The volume (in ml) of base required to titrate the aliquot from pH 10 down to pH 2.7.

$V_{bb}$=The volume (in ml) of base required to titrate 20 ml of synthetic urine from pH 10 down to pH 2.7.

$N_b$=The normality (in meq/ml) of the base (nominally 0.10 meq/ml).

3. The amount of polymerized neutralized acid moieties (e.g., sodium acrylate) (in mm) in the original supernatant aliquot ($M_b$) is given by:

$$M_b = M_t - M_a$$

4. The total amounts of polymerized acid moieties ($W_a$) and polymerized neutralized acid moieties ($W_b$) (e.g., acrylic acid plus sodium acrylate) extracted (in mg) are given by:

$$W_a = M_a E_a D \text{ and } W_b = M_b E_b D$$

where:

$E_a$=The equivalent weight of acid moiety in polyacid moiety (e.g., acrylic acid in polyacrylic acid=72 meq/mg).

$E_b$=The equivalent weight of neutralized acid moiety in neutralized polyacid moiety (e.g., sodium acrylate in sodium polyacrylate=94 meq/mg).

D=The dilution factor (75 ml/20 ml=3.75).

5. The percent extractable polymer in the hydrogel-forming polymer sample (e) is given by:

$$e = [(W_a + W_b)100]/W \text{ percent}$$

where: W=The sample weight in mg.

Absorbency Under Load (AUL)

The ability of a superabsorbent material to absorb a liquid while under a load is well known to those skilled in the art of superabsorbent polymers and determined as follows. A Demand Absorbency Tester (DAT) is used, which is similar to the GATS (Gravimetric Absorbency Test System), available from M/K Systems, Danners, Mass. USA, as well as the system described by Lichstein at pages 129-142 of the INDA Technological Symposium Proceedings, March 1974. A porous plate is used, having ports confined within a 2.5 centimeter diameter area and covered by the Absorbency Under Load (AUL) apparatus. An electrobalance is used to measure the flow of fluid into the superabsorbent particles. For this test, the fluid employed is an aqueous solution containing 0.9 weight percent sodium chloride used at room temperature.

The AUL apparatus used to contain the superabsorbent particles includes a cylinder made from 1 inch (2.54 centimeters) inside diameter thermoplastic tubing which is machined-out slightly to be sure of concentricity. A 100 mesh stainless steel wire cloth is adhered on the bottom of cylinder by means of an adhesive. Alternatively, the stainless steel wire cloth can be fused to the bottom of cylinder by heating the wire cloth in a flame until red hot, after which the cylinder is held onto the cloth until cooled. A soldering iron can be used to touch up the seal if unsuccessful or if it breaks. Care must be taken to maintain a flat, smooth bottom, and not distort the inside of the cylinder. A 4.4 gram piston is made from 1 inch diameter solid material (e.g., PLEXIGLAS® and is machined to closely fit without binding in the cylinder. The piston is used to provide the restraining load of 0.01 pound per square inch. A weight is used to provide the greater degrees of restraining load. As discussed above, the greater restraining loads are 0.29 pound per square inch, 0.57 pound per square inch, and 0.90 pound per square inch. Accordingly, a 100, 200, and 317 gram weight is used to provide the respective restraining loads (in addition to the 4.4 gram piston. A sample of superabsorbent particles weighing 0.160 (.+−0.0.005) gram is utilized for testing AUL. The sample is taken from granules which are pre-screened through US standard 30 mesh and retained on US standard 50 mesh (300-600 microns). The particles, when tested, have a moisture content of less than about 5 weight percent.

This test is initiated by placing a 3 centimeter diameter GF/A glass filter paper onto the plate. The paper is sized to be larger than the internal diameter and smaller than the outside diameter of the cylinder to ensure good contact while eliminating evaporation over the ports of the DAT and then allowing saturation to occur. The SAP particles are weighed on weighing paper and placed on the wire cloth at the bottom of the AUL apparatus. The AUL apparatus is shaken to level the particles on the wire cloth. Care is taken to be sure no particles are clinging to the wall of the cylinder. After carefully placing, without pressing, the piston and, optionally, the weight on the particles in the cylinder, the AUL apparatus is placed on the glass filter paper. The amount of fluid picked up is monitored as a function of time either directly by hand, with a strip-chart recorder, or directly into a data acquisition or personal computer system.

The amount (in grams) of fluid picked up after 60 minutes, divided by the weight of the sample (0.160 gram), is the AUL value in grams of fluid picked up per gram of sample (g/g). The rate of fluid picked up can also be measured. Two checks can be made to ensure the accuracy of the instantaneous final readout. First, the height the piston rises multiplied by the cross-sectional area of the cylinder should nearly equal the amount of fluid picked up. Second, the AUL apparatus can be weighed before and after the test and the difference in weight should nearly equal the fluid picked up. A minimum of three tests are performed on a given sample and averaged to assign an AUL value.

Gel Bed Permeability (GBP)

Figure 1:
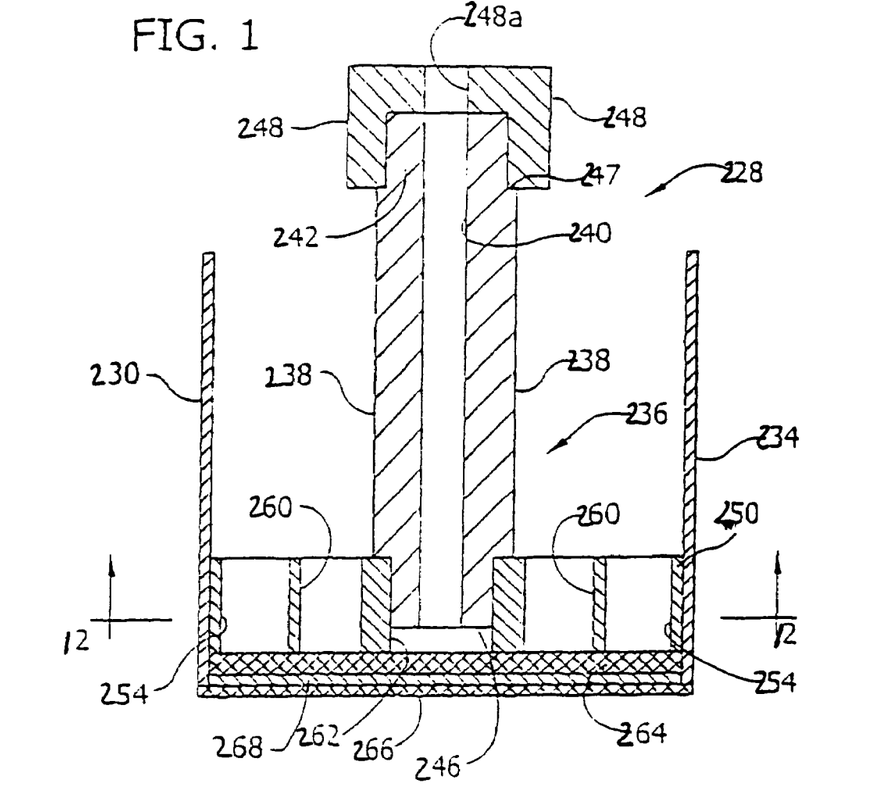
FIG. 1 is an illustration of equipment for determining the Gel Bed Permeability (GBP) value of a superabsorbent polymer.
Figure 2:
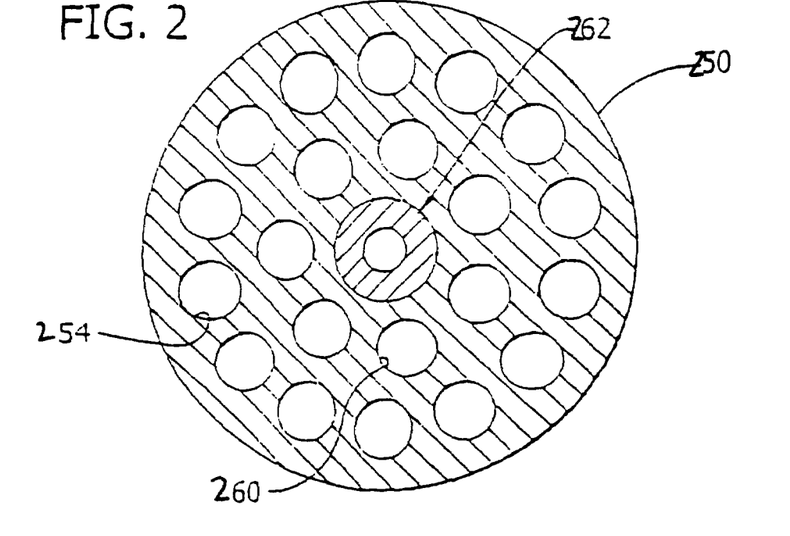
FIG. 2 is a cross-sectional view of the piston head taken along line 12-12 of FIG. 1.
Figure 4:
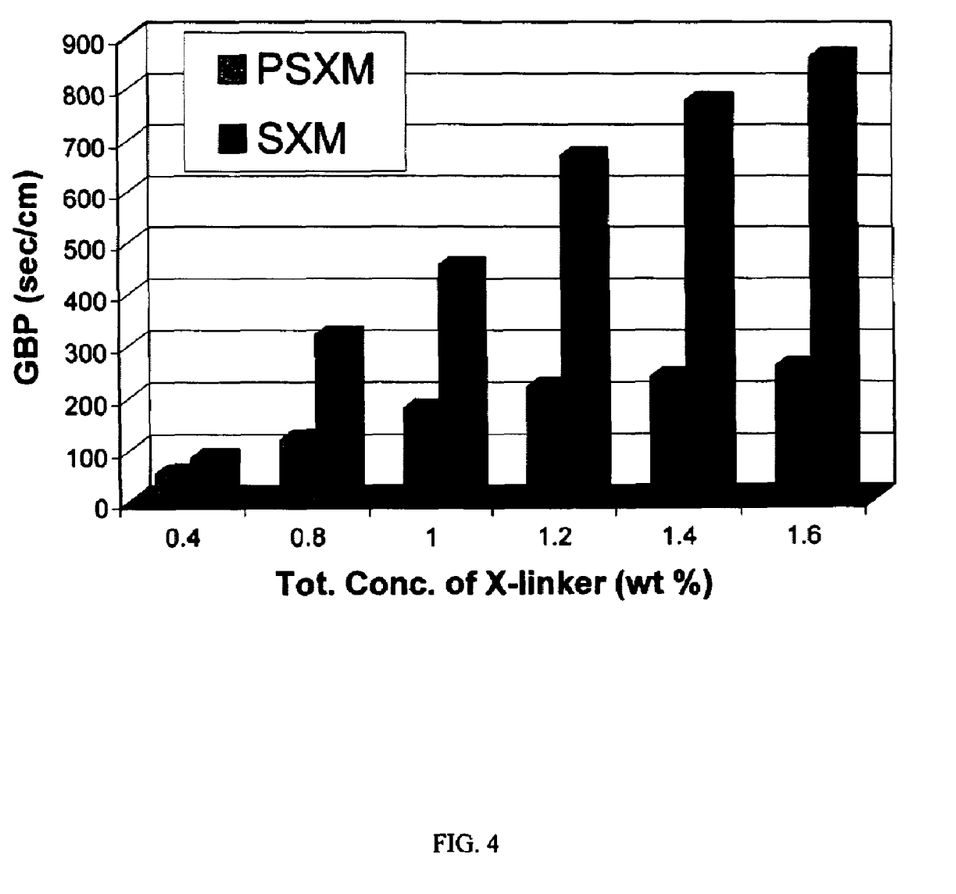
FIG. 4 is a bar chart depicting the relationship of GBP and total concentration of crosslinker.

A suitable piston/cylinder apparatus for performing the GBP test is shown in FIGS. 1 and 2. Referring to FIG. 1, apparatus 228 consists of a cylinder 234 and a piston generally indicated as 236. As shown in FIG. 4, piston 236 consists of a cylindrical LEXAN® shaft 238 having a concentric cylindrical hole 240 bored down the longitudinal axis of the shaft. Both ends of shaft 238 are machined to provide ends 242 and 246. A weight, indicated as 248, rests on end 242 and has a cylindrical hole 248a bored through the center thereof. Inserted on the other end 246 is a circular piston head 250. Piston head 250 is sized so as to vertically move inside cylinder 234. As shown in FIG. 2, piston head 250 is provided with inner and outer concentric rings containing seven and fourteen approximately 0.375 inch (0.95 cm) cylindrical holes, respectively, indicated generally by arrows 260 and 254. The holes in each of these concentric rings are bored from the top to bottom of piston head 250.

Piston head 250 also has cylindrical hole 262 bored in the center thereof to receive end 246 of shaft 238.

Attached to the bottom end of cylinder 234 is a No. 400 mesh stainless steel cloth screen 266 that is biaxially stretched to tautness prior to attachment. Attached to the bottom end of piston head 250 is a No. 400 mesh stainless steel cloth screen 264 that is biaxially stretched to tautness prior to attachment. A sample of superabsorbent material indicated as 268 is supported on screen 266.

Cylinder 234 is bored from a transparent LEXAN® rod or equivalent and has an inner diameter of 6.00 cm (area=28.27 cm$^2$), a wall thickness of approximately 0.5 cm, and a height of approximately 5.0 cm. Piston head 250 is machined from a LEXAN® rod. It has a height of approximately 0.625 inches (1.59 cm) and a diameter sized such that it fits within cylinder 234 with minimum wall clearances, but still slides freely. Hole 262 in the center of the piston head 250 has a threaded 0.625 inch (1.59 cm) opening (18 threads/inch) for end 246 of shaft 238. Shaft 238 is machined from a LEXAN® rod and has an outer diameter of 0.875 inches (2.22 cm) and an inner diameter of 0.250 inches (0.64 cm). End 146 is approximately 0.5 inches (1.27 cm) long and is threaded to match hole 262 in piston head 250. End 242 is approximately 1 inch (2.54 cm) long and 0.623 inches (1.58 cm) in diameter, forming an annular shoulder to support the stainless steel weight 248. The annular stainless steel weight 248 has an inner diameter of 0.625 inches (1.59 cm), so that it slips onto end 242 of shaft 238 and rests on the annular shoulder formed therein. The combined weight of piston 236 and weight 248 equals approximately 596 g, which corresponds to a pressure of 0.30 psi (20,685 dynes/cm$^2$) for an area of 28.27 cm$^2$.

When solutions flow through the piston/cylinder apparatus, the cylinder 234 generally rests on a 16 mesh rigid stainless steel support screen (not shown) or equivalent.

The piston and weight are placed in an empty cylinder to obtain a measurement from the bottom of the weight to the top of the cylinder. This measurement is taken using a caliper readable to 0.01 mm. This measurement will later be used to calculate the height of the gel bed. It is important to measure each cylinder empty and keep track of which piston and weight were used. The same piston and weight should be used for measurement when gel is swollen.

The superabsorbent layer used for GBP measurements is formed by swelling approximately 0.9 g of a superabsorbent material in the GBP cylinder apparatus (dry polymer should be spread evenly over the screen of the cylinder prior to swelling) with an aqueous 0.9 weight percent sodium chloride solution for a time period of about 60 minutes. The sample is taken from superabsorbent material which is prescreened through U.S. standard #30 mesh and retained on U.S. standard #50 mesh. The superabsorbent material, therefore, has a particle size of between 300 and 600 microns. The particles may be pre-screened by hand or automatically pre-screened with, for example, a Ro-Tap Mechanical Sieve Shaker Model B available from W. S. Tyler, Inc., Mentor, Ohio.

At the end of this period, the cylinder is removed from the fluid and the piston weight assembly is placed on the gel layer. The thickness of the swollen superabsorbent layer is determined by measuring from the bottom of the weight to the top of the cylinder with a micrometer. The value obtained when taking this measurement with the empty cylinder is subtracted from the value obtained after swelling the gel. The resulting value is the height of the gel bed H.

The GBP measurement is initiated by adding the Nacl solution to cylinder 234 until the solution attains a height of 4.0 cm above the bottom of superabsorbent layer 268. This solution height is maintained throughout the test. The quantity of fluid passing through superabsorbent layer 268 versus time is measured gravimetrically. Data points are collected every second for the first two minutes of the test and every two seconds for the remainder. When the data are plotted as quantity of fluid passing through the bed versus time, it becomes clear to one skilled in the art when a steady flow rate has been attained. Only data collected once the flow rate has become steady is used in the flow rate calculation. The flow rate, Q, through the superabsorbent layer 268, is determined in units of gm/sec by a linear least-square fit of fluid passing through the superabsorbent layer 268 (in grams) versus time (in seconds).

Permeability in cm$^2$ is obtained by the following equation:

$$K=[Q*H*Mu)]/[A*Rho*P]$$

where K=Gel Bed Permeability (cm$^2$); Q=flow rate (g/sec);

H=height of gel bed (cm); Mu=liquid viscosity (poise);

A=cross-sectional area for liquid flow (cm$^2$); Rho=liquid density (g/cm$^3$); and P=hydrostatic pressure (dynes/cm$^2$) [normally 3923 dynes/cm$^2$].

EXAMPLES

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Preparation of Superabsorbent Precursor A monomer mixture containing acrylic acid, de-ionized water, polyethylene glycol diacrylate (Mw 300), and sodium hydroxide (NaOH) was prepared, and cooling down to 5° C., then sparged with nitrogen for 5-10 minutes. The monomer mixture will be polymerized as soon as initiators such as sodium persulfate and hydrogen peroxide was added into the reactive solution. The resulting poly(acrylic acid) hydrogel was cut into small pieces, and extruded through Hobart meat grinder. The gel (150 g) then was mixed with 150 grams of the wet chitosan-polyamine particles (<300 microns in size, 30% chitosan mixed with 70% deionized water). The chitosan-polymaine is available from Vanson as a standard grade chitosan. The resulting mixture was extruded three times using Hobart meat grinder, then dried at 110° C. forced-air oven for 60 minute, and ground and sized through sieves to obtain the desired particles sizes having a size of about 300 microns.

Surface treatment of Superabsorbent Polymers

A surface treating solution was prepared by admixing 0.4 g of Ethylene Glycol Diglycidyl Ether (EGDGE), 4 grams Acetone and 4 grams de-ionized water. 100 grams of dry superabsorbent precursors were placed in Kitchen-aid mixer, and stirred at a sufficient speed to spread the SAP particle in Kitchen-aid, then 8.4 grams of the surface-treating solution was driven out by air-forced spray gun, and spread to the superabsorbent particle. These coated superabsorbent particles was dried at 100° C. for 60 minute, and ground and sized through sieves to obtain the desired particles sizes.

TABLE 1

Examples and physical data of superabsorbent polymer

| Example | Degree of preneutralization of PAA (mole %) | Ratio of Chitosan/PAA by wt % | % moisture | CRC (g/g) | Residual Monomer (ppm) | 1 hr extractable (%) | pH |
|---|---|---|---|---|---|---|---|
| 1 | 0 | 1:1 | 2.9 | 24.7 | 410 | 2.8 | 5.14 |
| 2 | 10 | 1:1 | 2.8 | 30.3 | 606 | 5.5 | 5.3 |
| 3 | 20 | 3:2 | 3.0 | 33.2 | 544 | 4.3 | 5.5 |
| 4 | 35 | 2:1 | 2.7 | 34.8 | 580 | 5.8 | 5.65 |
| 5 | 50 | 3:1 | 2.9 | 35.2 | 632 | 7.8 | 6.0 |

TABLE 2

Examples and data of surface crosslinked Superabsorbent Polymers.

| Example | Degree of Preneutralization of PAA (mole %) | Ratio of Chitosan/PAA by wt % | CRC (g/g) | 0.3 AUL (g/g) | 0.9 AUL (g/g) | Density (g/cc) | GBP ($\times 10^{-9}$ sec/cm$^2$) |
|---|---|---|---|---|---|---|---|
| 6 | 0 | 1:1 | 20.8 | 21.9 | 15.5 | 0.48-0.52 | 700 |
| 7 | 15 | 1:1 | 26.5 | 24.48 | 15.6 | 0.52-0.56 | 450 |

Figure 3:
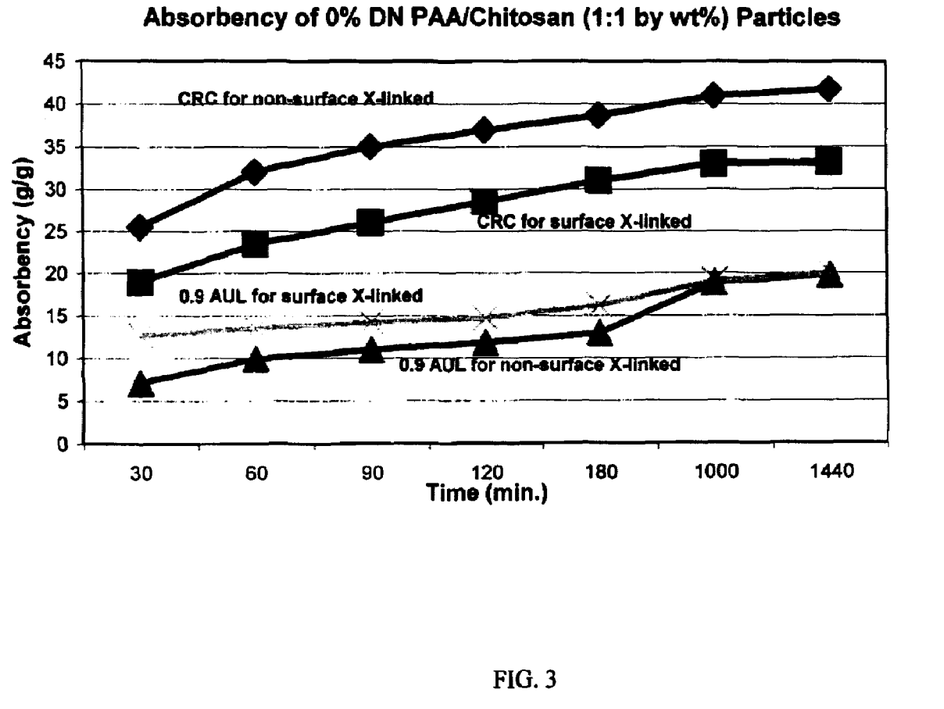
FIG. 3 is a graph depicting the relationship of Absorbency and Time.

In FIG. 3, note is taken that the superabsorbent is made of a polyacrylic acid having 0% neutralization that is mixed with the chitosan in a 1:1 ratio as discussed in the section Preparation of Superabsorbent Precursor. The resulting superabsorbent is neutralized to about 30 mole % by the presence of the chitosan and an aqueous solution. The graphs in FIG. 3 show the superabsorbent, surface crosslinked and non-surface crosslinked, continues to increase in absorbency over a period of 1440 minutes, i.e. 1 day.

FIG. 4 shows the positive impact of adding more crosslinking material to increase the permeability of the superabsorbent. PSXM indicates no crosslinking agent in the superabsorbent and SXM indicates addition of the crosslinking agent.

What is claimed is:

1. Superabsorbent polymer particles consisting essentially of:
    a) a polymeric resin composition comprising
        i) from about 55 to about 99.9% by weight of polymerizable unsaturated acid group containing monomers;
        ii) from about 0.001 to about 5.0% by weight of the polymerizable unsaturated acid group containing monomers of an internal crosslinking agent;
        iii) from 0 to about 25% by weight of the polymerizable unsaturated acid group containing monomers of a pre-neutralizing agent; wherein the polymeric resin composition is preneutralized from 0 to about 50 mole %; wherein the polymeric resin composition is formed into particles, and
    b) a water swellable, water-insoluble aminopolysaccharide polymer particles; wherein when the superabsorbent polymer is contacted with an aqueous solution, the polymeric resin is neutralized by the aminopolysaccharide polymer so that the superabsorbent polymer has a degree of neutralization of about 20 mole % or more than the preneutralization degree of the polymeric resin composition wherein the polymeric resin composition particles and aminopolysaccharide polymer particles are combined to form the superabsorbent polymer particles.

2. The superabsorbent polymer particles of claim 1 having a gel bed permeability as measured by the Gel Bed Permeability Test on superabsorbent polymer particles having a particle size of from about 300 microns to about 600 microns of about $100 \times 10^{-9}$ cm$^2$ or greater.

3. The superabsorbent polymer particles of claim 1 having a liquid capacity as measured by the Centrifuge Retention Capacity Test on superabsorbent polymer particles having a particle size of from about 300 microns to about 600 microns of about 20 g/g or greater.

4. The superabsorbent polymer particles of claim 1 having a liquid capacity as measured by the Centrifuge Retention Capacity Test on superabsorbent polymer particles having a particle size of from about 300 microns to about 600 microns of about 25 g/g or greater.

5. The superabsorbent polymer particles of claim 1 having a Gel Bed Permeability as measured by the Gel Bed Permeability Test on superabsorbent polymer particles having a particle size of from about 300 microns to about 600 microns of about $200 \times 10^{-9}$ cm$^2$ or greater.

6. The superabsorbent polymer particles of claim 1 having a Gel Bed Permeability as measured by the Gel Bed Permeability Test on superabsorbent polymer particles having a particle size of from about 300 microns to about 600 microns of about $300 \times 10^{-9}$ cm$^2$ or greater.

7. The superabsorbent polymer particles of claim 1 further comprising from about 0.001 to about 5.0% by weight of the dry superabsorbent polymer of surface crosslinking agent applied to the particle surface.

8. The superabsorbent polymer particles of claim 1 is a mixture of aminopolysaccharide and the polymeric resin in a weight ratio of about 5:95 to about 95:5, and the aminopolysaccharide is neutralized from 0 to about 25 mole %.

9. The superabsorbent polymer particles of claim 1 wherein the aminopolysaccharide polymer is a chitosan polyamine.

10. The superabsorbent polymer particles of claim 1 further comprising a surface treatment.

11. The superabsorbent polymer particles of claim 10 having an Absorbency Under Load at 0.9psi as measured by the Absorbency Under Load Test on superabsorbent polymer particles having a particle size of from about 300 microns to about 600 microns of about 15 or more and Gel Bed Permeability as measured by the Gel Bed Permeability Test on superabsorbent polymer particles having a particle size of from about 300 microns to about 600 microns of about $450 \times 10^{-9}$ cm$^2$ or greater.

12. Superabsorbent polymer particles consisting essentially of:
    a) from about 1 to about 99% by weight of crosslinked polyacrylic acid resin wherein the polyacrylic acid resin is preneutralized from 0 to about 50 mole %; and
    b) from about 1 to about 99% by weight of water swellable, water-insoluble aminopolysaccharide polymer particles wherein when the superabsorbent polymer particles are contacted with an aqueous solution, the crosslinked polyacrylic acid resin is neutralized by the aminopolysaccharide polymer so the superabsorbent polymer has a degree of neutralization of about 20 mole % or more than the preneutralization degree of the polyacrylic acid resin and wherein the polymeric resin composition particles and aminopolysaccharide polymer particles are combined to form the superabsorbent polymer particles and said superabsorbent polymer particles has a particle size from about 300 micron to about 600 microns.

13. The superabsorbent polymer particles of claim 12 wherein the crosslinked polyacrylic acid has a degree of neutralization of 30 mole % or more.

14. The superabsorbent polymer particles of claim 12 having a liquid capacity as measured by the Centrifuge Retention Capacity Test on superabsorbent polymer particles having a particle size of from about 300 microns to about 600 microns of about 20 g/g or greater.

15. The superabsorbent polymer particles of claim 12 having a liquid capacity as measured by the Centrifuge Retention Capacity Test on superabsorbent polymer particles having a particle size of from about 300 microns to about 600 microns of about 25 g/g or greater.

16. The superabsorbent polymer particles of claim 12 having a Gel Bed Permeability as measured by the Gel Bed Permeability Test on superabsorbent polymer particles having a particle size of from about 300 microns to about 600 microns of about $200 \times 10^{-9}$ cm$^2$ or greater.

17. The superabsorbent polymer particles of claim 12 having a Gel Bed Permeability as measured by the Gel Bed Permeability Test on superabsorbent polymer particles having a particle size of from about 300 microns to about 600 microns of about $300 \times 10^{-9}$ cm$^2$ or greater.

18. The superabsorbent polymer particles of claim 12 further comprising from about 0.001 to about 5.0% by weight of the dry superabsorbent polymer of surface crosslinking agent applied to the particle surface.

19. The superabsorbent polymer particles of claim 18 having an Absorbency Under Load at 0.9psi as measured by the Absorbency Under Load Test on superabsorbent polymer particles having a particle size of from about 300 microns to about 600 microns of about 15 or more and Gel Bed Permeability as measured by the Gel Bed Permeability Test on superabsorbent polymer particles having a particle size of from about 300 microns to about 600 microns of about $450 \times 10^{-9}$ cm$^2$ or greater.

20. The superabsorbent polymer particles of claim 10 wherein the aminopolysaccharide polymer is chitosan.

21. An absorbent composite comprising superabsorbent polymer particles consisting essentially of:
    a) a polymeric resin composition comprising
        i) from about 55 to about 99.9% by weight of polymerizable unsaturated acid group containing monomers;
        ii) from about 0.001 to about 5.0% by weight of the polymerizable unsaturated acid group containing monomers of internal crosslinking agent;
        iii) from 0 to 25% by weight of the polymerizable unsaturated acid group containing monomers of a pre-neutralizing agent; wherein the polymeric resin composition is preneutralized from 0 to about 50 mole %; and
    b) a water swellable, water-insoluble aminopolysaccharide polymer;
    wherein when the superabsorbent polymer is contacted with an aqueous solution, the polymeric resin composition is neutralized by the water swellable, water-insoluble aminopolysaccharide polymer and the superabsorbent polymer has a degree of neutralization of about 20 mole % or more than the preneutralized amount of the polymeric resin composition.

22. The absorbent composite of claim 21 wherein the superabsorbent polymer particles have a liquid capacity as measured by the Centrifuge Retention Capacity Test on superabsorbent polymer particles having a particle size of from about 300 microns to about 600 microns of about 20 g/g or greater.

23. The absorbent composite of claim 21 wherein the superabsorbent polymer particles have a liquid capacity as measured by the Centrifuge Retention Capacity Test on superabsorbent polymer particles having a particle size of from about 300 microns to about 600 microns of about 25 g/g or greater.

24. The absorbent composite of claim 21 wherein the superabsorbent polymer particles have a Gel Bed Permeability as measured by the Gel Bed Permeability Test on superabsorbent polymer particles having a particle size of from about 300 microns to about 600 microns of about $200 \times 10^{-9}$ cm$^2$ or greater.

25. The absorbent composite of claim 21 wherein the superabsorbent polymer particles have a Gel Bed Permeability as measured by the Gel Bed Permeability Test on superabsorbent polymer particles having a particle size of from about 300 microns to about 600 microns of about $300 \times 10^{-9}$ cm$^2$ or greater.

26. The absorbent composite of claim 21 wherein the superabsorbent polymer particles further comprise from about 0.001 to about 5.0% by weight of the dry superabsorbent polymer of surface crosslinking agent applied to the particle surface.

27. The absorbent composite of claim 21 wherein the superabsorbent polymer particles have an Absorbency Under Load at 0.9psi as measured by the Absorbency Under Load Test on superabsorbent polymer particles having a particle size of from about 300 microns to about 600 microns of about 15 or more and Gel Bed Permeability as measured by the Gel Bed Permeability Test of on superabsorbent polymer particles having a particle size of from about 300 microns to about 600 microns of about $450 \times 10^{-9}$ cm$^2$ or greater.

28. The absorbent composite of claim 21 wherein the aminopolysaccharide polymer is a chitosan.

29. An absorbent composite of claim 21 further comprising a mixture of fibers.

30. A process for the continuous production of superabsorbent polymer composition for absorbing aqueous or serous fluids, as well as blood, comprising the steps of:
   a) preparing a polymeric resin composition by reacting
      i) from about 55 to about 99.9 00 by weight of polymerizable unsaturated acid group containing monomers; and
      ii) from about 0.001 to about 5.0% by weight of polymerizable unsaturated acid group containing monomers of internal crosslinking agent; and
      iii) from 0 to about 25% by weight of polymerizable unsaturated acid group containing monomers of a preneutralizing agent; wherein the polymeric resin composition is preneutralized from 0 to about 50 mole %; and
   b) preparing an aqueous solution containing a water swellable, water-insoluble aminopolysaccharide polymer;
   c) mixing the polymeric resin composition with the aqueous solution containing aminopolysaccharide polymer to form the superabsorbent polymer; and
   d) drying the superabsorbent polymer wherein when the superabsorbent polymer is contacted with an aqueous solution, the polymeric resin composition is neutralized by the aminopolysaccharide polymer so the polymeric resin composition is neutralized by the water swellable, water-insoluble aminopolysaccharide polymer such that the superabsorbent polymer has a degree of neutralization of about 20 mole % of more than the preneutralization degree of the polymeric resin wherein the ratio of the superabsorbent polymer composition has a mean particle size of about 300 microns.

31. The process of claim 30 wherein the aminopolysaccharide polymer is chitosan.

* * * * *

UNITED STATES PATENT AND TRADEMARK OFFICE
CERTIFICATE OF CORRECTION

PATENT NO. : 7,291,674 B2 Page 1 of 1
APPLICATION NO. : 10/695060
DATED : November 6, 2007
INVENTOR(S) : Seungkoo Kang and Scott J. Smith It is certified that error appears in the above-identified patent and that said Letters Patent is hereby corrected as shown below:

Column 6,
Line 41, "EDGDE" should be replaced by --EGDGE--.

Line 44, "EDGDE" should be replaced by --EGDGE--.

Line 46, "EDGDE" should be replaced by --EGDGE--.

Line 58, "EDGDE" should be replaced by --EGDGE--.

Line 61, "EDGDE" should be replaced by --EGDGE--.

Column 9,
Line 54, "clay" should be replaced by --Clay--.

Column 19,
Line 7, "99.9 00" should be replaced by --99.9%--.

Column 20,
Line 11, "20 mole % of" should be replaced by --20 mole % or--.

Signed and Sealed this

Eighth Day of July, 2008

JON W. DUDAS
*Director of the United States Patent and Trademark Office*